United States Patent
Leconte et al.

(10) Patent No.: US 12,181,266 B2
(45) Date of Patent: Dec. 31, 2024

(54) FACILITY AND METHOD FOR MEASURING THE THICKNESS OF THE WALLS OF GLASS CONTAINERS

(71) Applicant: TIAMA, Vourles (FR)

(72) Inventors: Marc Leconte, Loire sur Rhone (FR); Pierre-Yves Solane, Lyons (FR)

(73) Assignee: TIAMA, Saint-Genis-Laval (FR)

(*) Notice: Subject to any disclaimer, the term of this patent is extended or adjusted under 35 U.S.C. 154(b) by 232 days.

(21) Appl. No.: 17/626,167

(22) PCT Filed: Jul. 10, 2020

(86) PCT No.: PCT/FR2020/051257
§ 371 (c)(1),
(2) Date: Jan. 11, 2022

(87) PCT Pub. No.: WO2021/009456
PCT Pub. Date: Jan. 21, 2021

(65) Prior Publication Data
US 2022/0244039 A1 Aug. 4, 2022

(30) Foreign Application Priority Data
Jul. 12, 2019 (FR) .................................. 19 07877

(51) Int. Cl.
*G01B 11/06* (2006.01)
*G01N 21/90* (2006.01)
*G01N 33/38* (2006.01)

(52) U.S. Cl.
CPC ........... *G01B 11/06* (2013.01); *G01N 33/386* (2013.01); *G01N 21/90* (2013.01)

(58) Field of Classification Search
CPC ....... G01B 11/06; G01N 33/386; G01N 21/90
See application file for complete search history.

(56) References Cited

U.S. PATENT DOCUMENTS 3,356,212 A * 12/1967 Landin .................... B07C 5/126
209/526
3,535,522 A * 10/1970 Hart ........................ G01B 11/06
374/7

(Continued)

FOREIGN PATENT DOCUMENTS

EP 0 643 297 3/1995
EP 1 020 703 7/2000

(Continued)

OTHER PUBLICATIONS

Crystran, "Silica Glasss (SiO2) Optical material", Dec. 12, 2016, https://www. https://www.crystran.co.uk/optical-materials/silica-glass-sio2.

*Primary Examiner* — Tri T Ton
*Assistant Examiner* — Jarreas Underwood
(74) *Attorney, Agent, or Firm* — Bauer & Joseph

(57) ABSTRACT

A method for measuring the thickness of glass containers includes the following steps:
choosing to measure the radiation emitted by the container from a first side and a second side of the container diametrically opposite to each other;
choosing to measure the radiation emitted by the container in a first spectral band in a range between 2,800 nm and 4,000 nm and in a second spectral band;
simultaneously measuring, from each side of the container, the intensity of the radiation coming from the walls in the first spectral band and in the second spectral band; and
determining at least the thickness of the first wall and of the second wall ($2_2$), from the measurements of the intensity of the radiation coming from the first wall in the first and second spectral bands and from the second wall in the first and second spectral bands.

15 Claims, 4 Drawing Sheets

(56) References Cited

U.S. PATENT DOCUMENTS

| | | | | |
|---|---|---|---|---|
| 6,188,079 B1 * | 2/2001 | Juvinall | ............... | G01B 21/085 |
| | | | | 250/559.27 |
| 2017/0215231 A1 * | 7/2017 | Doerk | ................... | F24C 15/105 |
| 2019/0195619 A1 * | 6/2019 | Kress | ..................... | G01N 25/72 |

FOREIGN PATENT DOCUMENTS

| | | | | |
|---|---|---|---|---|
| EP | 2831541 B1 * | 4/2021 | ........... | B07C 5/3408 |
| FR | 2 842 301 | 1/2004 | | |
| JP | 2006133234 A * | 5/2006 | | |

* cited by examiner

[Fig. 1]
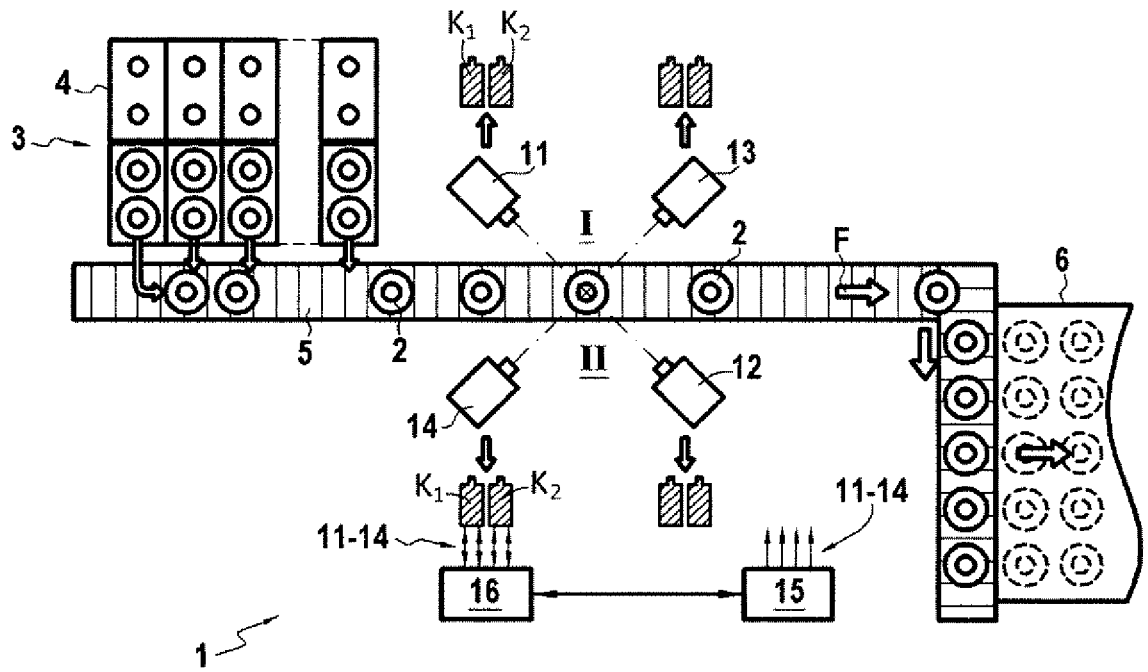
[Fig. 2]
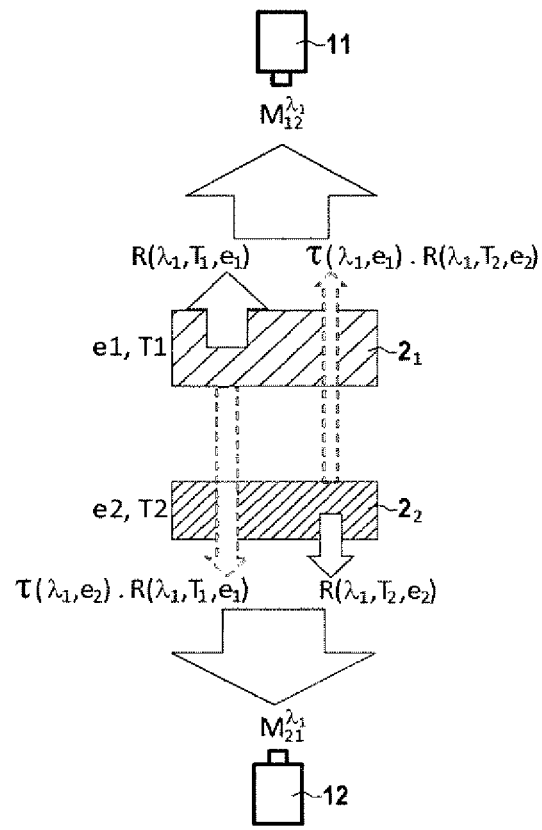

[Fig. 3]
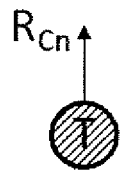
[Fig. 4]
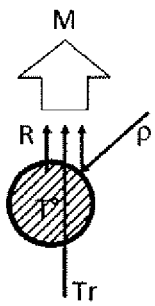
[Fig. 5]
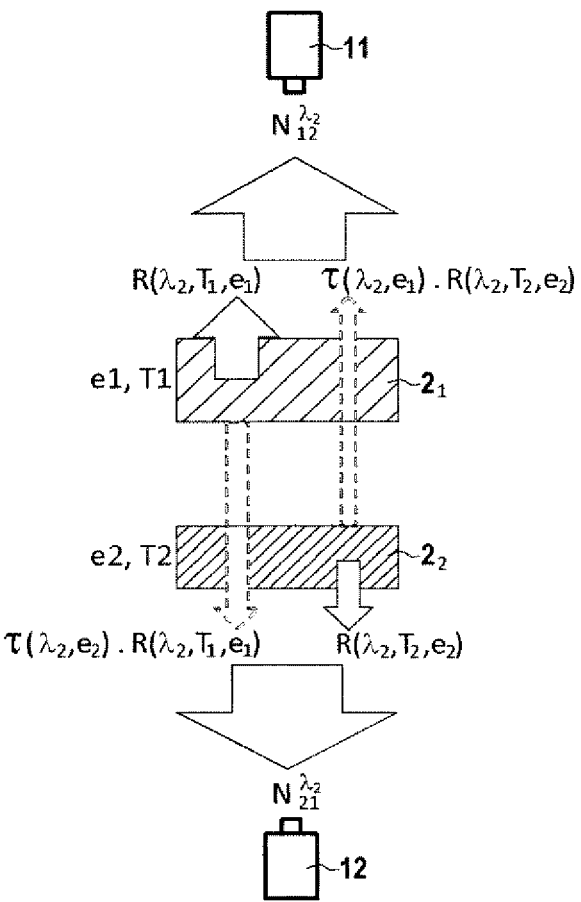

[Fig. 6]
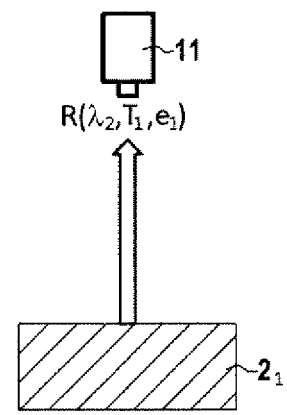
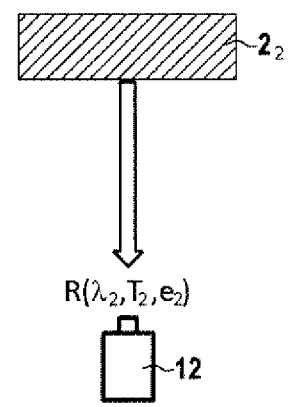
[Fig. 7]
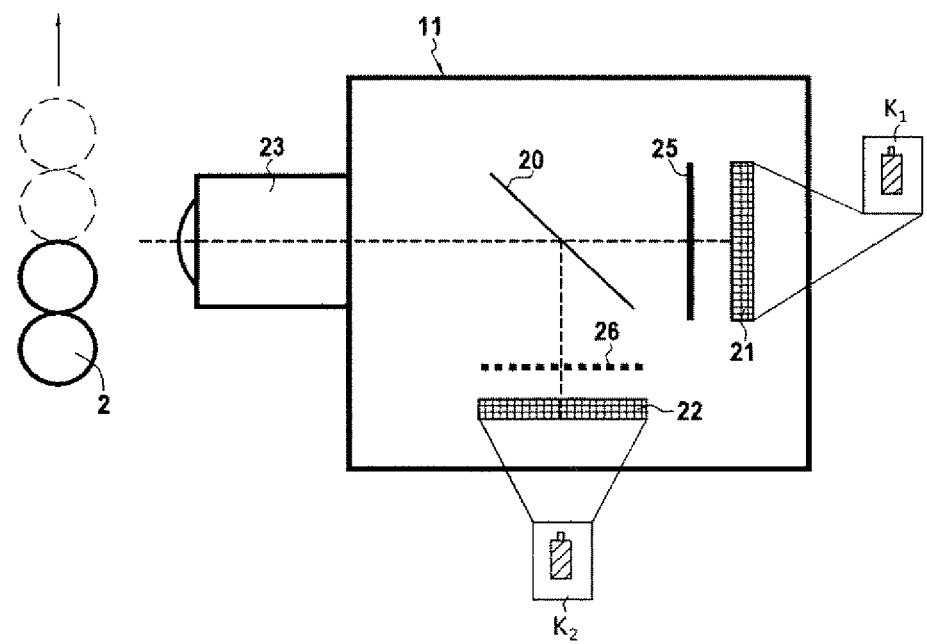

[Fig. 8]
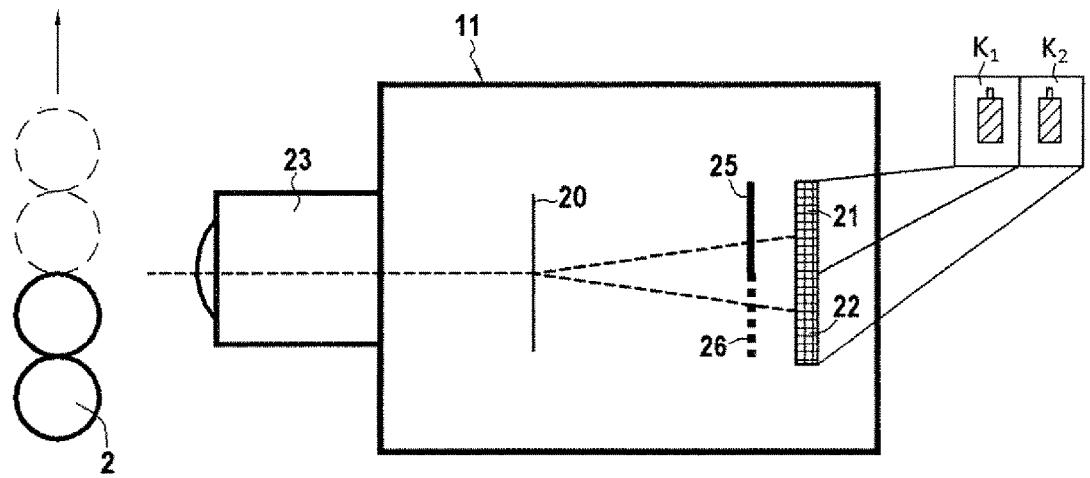
[Fig. 9]
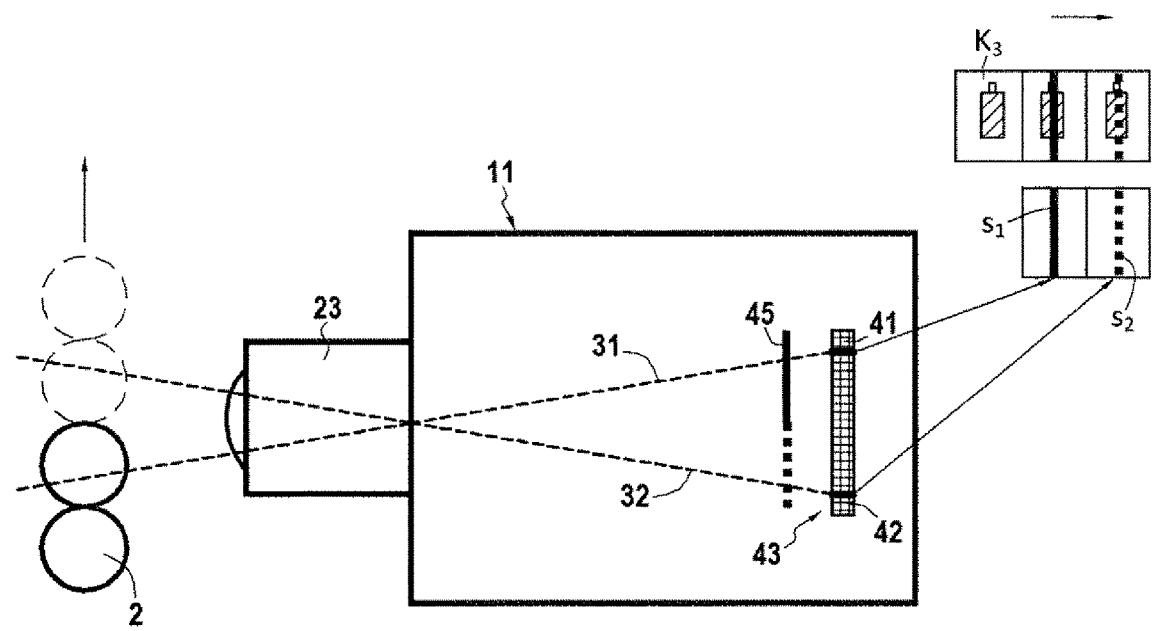

FACILITY AND METHOD FOR MEASURING THE THICKNESS OF THE WALLS OF GLASS CONTAINERS

TECHNICAL FIELD

The present invention relates to the technical field of the optical inspection of translucent or transparent containers or hollow objects having a high temperature.

The object of the invention is more specifically the high-speed optical inspection of objects such as glass bottles or flasks still hot exiting a manufacturing or forming machine. Thus, the object of the invention aims the inspection of objects in the hot sector of a manufacturing facility.

Conventionally, after melting the glass in a furnace around 1,600°, the molten glass is brought above the forming machines through channels called "front-core" channels. The facility also includes a distributor of gobs of molten glass or drops of malleable glass falling by gravity into each blank mold. This member thus forms drops of glass which are distributed in the direction of various independent forming sections by means of a set of guides called deliver guides. A machine called forming machine IS consists of different sections each equipped with at least one blanking cavity equipped with a blank mold, and with the same number of finishing cavities, each receiving a finishing mold in which the containers assume their final shape at high temperature. The 1, 2, 3 or 4 blank cavities of a section are loaded in turn in a predefined order in one, two, three or four drops of hot glass (around 1,200° C.) called gob. At the output of the forming machine, the containers still at high temperature, generally between 300° C. and 600° C., are picked up at their finish to be routed so as to constitute a line on a transport conveyor. The spacing between the containers is variable and imposed by the forming machine along its own center distance and the diameters of the containers. The transport conveyor brings the containers to travel successively in various treatment stations such as a spray hood for a surface treatment and an annealing furnace called an annealing lehr.

It appears interesting to identify a forming defect as early as possible at the output of the forming machine before the various treatment stations so as to be able to correct this defect as soon as possible at the forming machine. It is thus advantageous to detect in particular dimensional deviations or deformations of the containers which are directly related to settings of the forming method, in order to correct, in case of drift, the method as quickly as possible.

The control of the quality of such containers allows eliminating those which have defects that may affect their esthetic nature or, worse, constitute a real danger for the subsequent users. Thus, it appears necessary to control the quality of the thickness distribution of such containers so as to eliminate the containers having too small thicknesses or thickness differences in some areas that may affect the mechanical strength.

Indeed, the quality of the thickness distribution is a very important parameter because the thickness can be variable, too high or too low in different parts of the container. This thickness disparity is a problem because the produced items are potentially fragile. In addition, manufacturers are looking for the possibility of manufacturing lightened and thinned glass containers, therefore it is necessary to know how to properly distribute the glass. The manufacturing parameters which influence the glass distribution are known and numerous, it is necessary to control them. These in particular include, mentioned by way of known examples, the following parameters:

i) the loading parameters which comprise the velocity vector and the centering of the drop when it falls into the blank mold;
ii) the distribution of heat in the drop;
iii) the cooling of the molds.

To correctly act on the manufacturing parameters, it is necessary to know the distribution of glass in the containers immediately after the forming.

It should be understood that knowing the thickness distribution means knowing in absolute terms the thicknesses at different points of the container or, failing that, in relative terms, thickness deviations between different regions of the container. For example, a bottle is composed, from below upwards, of a bottom, a body connected to the bottom by the heel, then a neck connected to the body by a shoulder and finally a finish for the filling and the closing by a stopper, a cap or a lid. A glass distribution fault can be observed for example vertically, with an excess of glass at the bottom, and a thin glass at the shoulder. Faults in the horizontal distribution can also be observed for example with, at the level of the shoulder, more glass on one side than on the opposite side relative to the axis. This analysis not only of minimum and maximum values of the glass thickness, but also the distribution and vertical or horizontal deviations, as well as the location of the thin or thick areas, is significant to properly correct the method.

Prior Art

In the state of the art, various solutions using the infrared radiation emitted by the still hot containers have been proposed for their inspection at the output of the forming machine with a view to measuring the glass distribution.

For example, U.S. Pat. No. 3,535,522 describes a method for measuring the glass thickness of a container consisting in measuring the infrared radiation emitted by such a container at the output of the forming machine. The measurement of the infrared radiation is performed while the container is placed in a furnace in order to homogenize the temperature of the container to a determined value. Then, the container, still inside the furnace, is rotated about a vertical axis, in front of the optical axis of an infrared sensor which measures during one revolution, between 2.06 and 2.5μ or between 3.56 and 4.06μ, this radiation passing through the wall. Since the temperature is supposed to be made homogeneous thanks to the furnace, the perceived radiation variations are directly attributable to the thickness variations. This technique does not allow continuously controlling the containers and requires a handling of the containers leading to a slow method that may lead to deformations of the containers.

Patent EP 0 643 297 describes a device for performing an analysis and a diagnosis on a method for manufacturing glass products including a sensor sensitive to the infrared radiation emitted by the objects exiting the forming machine. This system also includes a digital processing device comparing the radiation with a mathematical reference model in order to determine the deviations existing in the distribution of the glass and/or the causes leading to the presence of thermal stresses in the container. In addition, this patent does not provide any indication of the means for obtaining a reference mathematical model.

It must be taken into account that such an infrared measuring device is therefore installed to observe the containers that travel on the output conveyor downstream (in the direction of travel) of the manufacturing machine, that is to say downstream of the last section, which is closest to the device. At the other end of the machine is therefore the most upstream section. Regarding the radiation emitted by the containers, it depends on many parameters, including the material distribution but also the temperature distribution. During the transfer of the containers between the section and the infrared measuring device, temperature transfers occur by radiation and conduction between the different portions of the container, along the direction of thermal balance, which may be called "spontaneous homogenization" of temperature, and a global cooling by radiation and convection, called "the cooling". The thermal state of the containers, therefore the temperature distribution in the material of the container when removed from the molds, is hereinafter called "initial conditions". The thermal state of the containers at the time of their inspection therefore depends on the one hand on said initial conditions and on the other hand on the spontaneous homogenization and on the cooling during transport, which are of course different based on the distance traveled by the container from its forming section to the inspection station.

In practice, according to this prior patent, radiation variations due to thermal stress or thickness deviations are detected, but it is impossible to determine a stress or thickness value, and even to determine whether a radiation variation is related to a thermal stress or material thickness deviation. It therefore appears in practice impossible to implement such a technique insofar as the measurement of the infrared radiation depends on numerous parameters such as those listed by way of non-limiting example below.

The intensity of the infrared radiation emitted by the hot containers strongly depends on the temperature according to the Stefan-Boltzmann law: $E = sT^{<A>4}$ where $E$=total amount of radiation emitted by an object in (watts m−2), $s$=the Stefan-Boltzmann constant=$5.67 \times 10-8$ Watts m−2K−4 and T=the temperature in degrees Kelvin (K).

The intensity of the infrared radiation emitted by the hot containers depends on the characteristics of these hot containers such as for example the size, the color, the shape and the composition of the glass.

It should be considered that the distance between the infrared sensor and the outlet of the molds is different from one mold to another so that the cooling time for each hot container is different, so that the hot containers have different temperatures when they pass in front of the infrared sensor. In other words, the intensity of the infrared radiation measured by the sensor depends on the origin of the manufacturing mold and more specifically on the position of this mold relative to the sensor.

At the output of the forming machine, the containers are slidably placed on a conveyor. This results in a difference in the positioning of the containers on the conveyor relative to the infrared measuring sensor, which is able to modify the measurements taken.

The forming temperature conditions as well as the interactions during the conveying of the containers may vary depending on the production conditions (start-up, incident, etc.) and on the environment (day/night, weather, air stream).

Since the radiation used according to EP 0 643 297 is a through radiation, the perceived radiation is that of the two combined walls.

It follows from the foregoing that many parameters influence the infrared radiation so that such a patent does not provide a solution for measuring the distribution of the glass thickness for containers at high temperature. This patent simply teaches the detection of the deviations in the glass distribution, provided that an operator verifies that the radiation deviations are due to the thickness. Only relative values of thicknesses or thermal stresses are estimated between different regions of the containers or between different containers and over short periods of time. This patent does not allow measuring in absolute value the glass thickness of the containers regardless of when the measurements were taken.

According to one variant, this patent provides for the implementation of an optical sensor for producing images of the glass products in order to obtain information on deflections and/or the distribution of glass. The information is compared with the data obtained from the sensor sensitive to the infrared radiation so as to be able to adjust the criteria according to which the data provided by the sensor sensitive to the infrared radiation have been analyzed. While the implementation of this variant provides a correction to the used criteria, it does not allow overcoming the drawbacks inherent in the method described in this patent and recalled above. Also, this solution does not allow measuring the thickness of the glass, neither in relative value nor in absolute value and as a result the distribution of the thickness over a wide area and even less over the entire container.

Patent EP 1 020 703 proposes to measure the glass thickness of a container from the infrared radiation consisting in measuring a first intensity of said radiation in a first spectral band at which the radiation is emitted by the material between the two outer and inner surfaces of the container. The first spectral band whose signal depends on both glass temperature and thickness is preferably between 0.4 and 1.1 microns. The method also consists in measuring a second intensity of said radiation in a second spectral band at which the radiation is emitted substantially entirely by a single outer surface of the container. According to this patent, the second spectral band at which the radiation depends only on the temperature, corresponding to a surface radiation, is preferably between 4.8 and 5 microns. The method consists in determining the thickness of the container between the outer and inner surfaces as a combined function of said first and second measured intensities. In other words, the thickness and the temperature are determined from the two radiation measurements taken in the first spectral band and in the second spectral band.

According to one variant illustrated in FIG. 3, this patent proposes to evenly distribute, over the circumference of the container, four cameras measuring the radiation in the second spectral band on which the radiation depends only on the temperature, and a pyrometer measuring the radiation in the first spectral band whose signal depends both on glass temperature and thickness.

It therefore appears that the exact thickness calculation is only possible for a point measured by the pyrometer and the camera. It results in a relationship established to know the thickness as a function of temperature. The other points measured by the other cameras are only estimated by an extrapolation by assuming that the thickness depends on the temperature according to a local mathematical model established in a location of the container. The assumption that the thickness is determined by a temperature measurement is false, unless the containers are homogeneous in temperature during forming, in other words, unless the initial temperature conditions are the same for the entire bottle.

In a complementary manner, it should be noted that in the first spectral band, the radiation of the container relative to the measurement point of the pyrometer comprises the radiation of the wall called front wall located on the side of the measurement point and depending on its thickness and its temperature, but also the radiation of the opposite wall called rear wall which emits towards the inside of the container and which passes through the front wall. This "rear radiation" is combined with the "front radiation" of the directly observed surface. The "front wall" only partially absorbs this radiation in the first spectral band. Thus, the perceived radiation depends on the thickness of the two walls and on the temperature of the two walls. In other words, the measurement of the radiation of the front wall does not allow measuring its thickness because the radiation is influenced by the rear wall.

Finally, it turns out that the method described by this patent is suitable for measuring the glass thickness of a container belonging to a family of limited tints. However, there is a need to be able to measure the thickness of glass containers with as many tints as possible.

Disclosure of the Invention

The object of the invention therefore aims to overcome the drawbacks of the prior techniques by proposing a new method for accurately measuring the thickness of the wall of high-temperature glass containers exiting the forming cavities, by taking into account the influence of the radiation that part of the wall brings to another part of the wall.

Another object of the invention is to propose a method for accurately measuring the thickness of the wall of glass containers having diversified tints.

To achieve such an objective, the method for measuring the thickness of high-temperature glass containers exiting the forming cavities comprises the following steps:
  choosing to measure the radiation emitted by the container from a first side and a second side of the container diametrically opposite to each other so as to take into account the radiation emitted by a first wall of the container located along the first side and a diametrically opposite second wall of the container located along the second side;
  choosing to measure the radiation emitted by the container in a first spectral band in a range between 2,800 nm and 4,000 nm and in a second spectral band, these two spectral bands being distinct and selected such that:
  on the one hand, the absorption of the radiation by the glass is different in the two spectral bands for the temperature of the containers;
  and on the other hand at least in the first spectral band, the absorption of the radiation by the glass is such that:
  the radiation measured from the first side of the container, coming from the first wall, is the sum of the radiation emitted by the first wall and of the radiation emitted by the second wall transmitted with absorption through the first wall, such that said combined radiation depends on the thicknesses and temperatures of the first and second walls;
  and the radiation measured from the second side of the container, coming from the second wall, is the sum of the radiation emitted by the second wall and of the radiation emitted by the first wall and transmitted with absorption through the second wall, such that said combined radiation depends on the thicknesses and temperatures of the first and second walls;
  simultaneously measuring, from the first side of the container, the intensity of the radiation coming from the first wall in the first spectral band and in the second spectral band and from the second side of the container, the intensity of the radiation coming from the second wall in the first spectral band and in the second spectral band;
  and determining at least the thickness of the first wall and of the second wall, from the measurements of the intensity of the radiation coming from the first wall in the first and second spectral bands and from the second wall in the first and second spectral bands, by taking into account in the intensity of the radiation in the first spectral band, the radiation emitted by a wall and the radiation transmitted with absorption, and coming from the other diametrically opposite wall.

In addition, the method according to the invention may further include in combination at least either or both of the following additional characteristics:
  in the second spectral band, the absorption of the radiation by the glass is different from that of the first spectral band, and is such that the radiation measured, on the one hand, from the first side of the container, coming from the first wall is the sum of the radiation emitted by the first wall and of the radiation emitted by the second wall and transmitted through the first wall, and on the other hand, from the second side of the container, coming from the second wall is the sum of the radiation emitted by the second wall and of the radiation emitted by the first wall and transmitted through the second wall, the combined radiation being dependent on the thicknesses of the walls and temperatures of the walls;
  the temperature of the first wall and of the second wall is also determined from the measurements of the intensity of the radiation of the first wall in the first and the second spectral band and of the second wall in the first and the second spectral band, by taking into account in the intensity of the radiation in the first spectral band, the radiation transmitted with absorption, and coming from the wall located on the other side.

Another object of the invention is to propose a method for accurately measuring the thickness of the wall of high-temperature glass containers for a wide range of glass tints including the white glass.

To achieve such an objective, the method according to which it is chosen to measure the radiation emitted by the container in the first spectral band in a range between 3,000 nm and 4,000 nm is carried out.

In addition, the method according to the invention may further include in combination at least either or both of the following additional characteristics:
  in the second spectral band, the absorption of the radiation by the glass is such that the radiation measured, on the one hand from the first side of the container, coming from the first wall, is the radiation emitted only by the surface of the first wall, and on the other hand from the second side of the container, coming from the second wall, is the radiation emitted only by the surface of the second wall, the radiation depending only on the temperature;
  determining the temperatures of the first wall and of the second wall from respectively the measurements of the intensity of the radiation of the first wall in the second spectral band and of the second wall in the second spectral band;
  choosing to measure the radiation emitted by the container in the second spectral band in a range between 1,100 nm and 2,600 nm;
  choosing to measure the radiation emitted by the container in the second spectral band in a range greater than 4,500 nm and preferably greater than 5,000 nm;

simultaneously measuring the radiation using at least two bispectral infrared cameras each delivering, for each container, at least two infrared images of the radiation of the wall of the container located in its field of observation.

Another object of the invention is to propose a facility for accurately measuring the thickness of the glass walls of the containers.

To achieve such an objective, the facility for measuring the thickness of the walls of the high-temperature glass containers exiting the forming cavities and moved along a translational path, includes:

at least a first and a second bispectral infrared camera disposed diametrically opposite to each other on either side of the path of the containers to take into account the radiation emitted by a first wall of the container located on a first side of the container and a second wall of the container located on a diametrically opposite second side, each camera delivering two infrared images of the radiation of the wall of the container located in its field of observation in a first spectral band in a range between 2,800 nm and 4,000 nm and in a second spectral band, these two spectral bands being distinct and selected such that:

on the one hand, the absorption of the radiation by the glass is different in the two spectral bands for the temperature of the containers;

and on the other hand at least in the first spectral band, the absorption of the radiation by the glass is such that:

the radiation measured from the first side of the container, coming from the first wall, is the sum of the radiation emitted by the first wall and of the radiation emitted by the second wall and transmitted with absorption through the first wall, such that said combined radiation depends on the thicknesses and temperatures of the first and second walls;

and the radiation measured from the second side of the container, coming from the second wall, is the sum of the radiation emitted by the second wall and of the radiation emitted by the first wall and transmitted with absorption through the second wall, such that said combined radiation depends on the thicknesses and temperatures of the first and second walls;

a system for driving the operation of the bispectral infrared cameras so as to acquire simultaneously, with the first camera, two images measuring the intensity of the radiation of the first wall in the first spectral band and in the second spectral band and with the second camera, two images measuring the intensity of the radiation of the second wall in the first spectral band and in the second spectral band;

and a computer configured to determine at least the thicknesses of the first wall and of the second wall, by analyzing the two images giving respectively the measurements of the intensity of the radiation coming from the first wall in the first and the second spectral band and the two images of the second wall in the first and the second spectral band, by taking into account in the intensity of the radiation in the first spectral band, the radiation emitted by a wall and the radiation transmitted with absorption, and coming from the wall located on the other side.

In addition, the facility according to the invention may include, according to one embodiment:

a bispectral infrared camera which includes:

a beam splitter, downstream of which the rays are separated into two distinct downstream beams;

downstream of the beam splitter, two distinct sensors or two sensor portions, placed in a plane or two image planes, each receiving one of the two distinct downstream beams, the first sensor or the first sensor portion receiving a first radiation beam in the first spectral band and the second sensor or the second sensor portion receiving a second radiation beam in the second spectral band;

the first and second beams being shaped upstream or downstream of the splitter by a lens forming, by optical conjugation on each image plane, an optical image of the container in respectively the first spectral band and in the second spectral band;

the first and/or the second beam being filtered by one or several optical filters selecting respectively the first spectral band and the second spectral band.

According to another embodiment, each bispectral infrared camera comprises:

a lens forming, by optical conjugation on a sensor plane, an optical image of a field through which a container passes;

two distinct linear sensor portions, with their support lines being vertical and disposed such that during the travel of a container in the field of a lens, a scan image is produced with each of the two linear sensor portions;

the first linear sensor portion receiving a first radiation beam portion in the first spectral band;

the second sensor portion receiving a second radiation beam portion in the second spectral band;

at least one optical filter disposed on the path of the light beams, to select the first spectral band and the second spectral band.

BRIEF DESCRIPTION OF THE DRAWINGS

FIG. 1 is a general top view showing an inspection facility in accordance with the invention suitable for measuring the thickness of the glass wall of the containers exiting a forming machine.

FIG. 2 is a schematic view explaining the principle of radiation of a container relative to measurement points located on each side of the container, in a first spectral band.

FIG. 3 is a view illustrating the thermal radiation of a black body.

FIG. 4 is a view illustrating the thermal radiation of a glass body.

FIG. 5 is a schematic view explaining the principle of radiation of a container relative to measurement points located on each side of the container, in a second spectral band.

FIG. 6 is a schematic view explaining the principle of radiation of a container relative to measurement points located on each side of the container, in a second spectral band sensitive only to the surface temperature of the glass wall.

FIG. 7 is a schematic view of an example of a bispectral infrared camera used within the framework of the invention.

FIG. 8 is a schematic view of another example of a bispectral infrared camera used within the framework of the invention.

FIG. 9 is a schematic view of another example of a bispectral infrared camera used within the framework of the invention.

DESCRIPTION OF THE EMBODIMENTS

In the description of the invention, a first spectral band $\lambda 1$ and a second spectral band $\lambda 2$ are used. A spectral band A is a wavelength interval centered on a value. Each working spectral band is chosen according to the invention or the variants, in specific wavelength ranges, which are wider wavelength intervals. This means that the wavelength interval of each working spectral band is included in an accurate wavelength range.

As emerges more specifically from FIG. 1, the object of the invention relates to a facility 1 for hot inspection of the glass containers 2 such as for example bottles or flasks, with a view to measuring the thickness of the glass wall of these containers. The facility 1 is placed so as to allow the inspection of the containers 2 exiting a manufacturing or forming machine 3 of all types known per se. At the output of the forming machine, the containers 2 have a high temperature typically of between 300° C. and 700° C.

The forming machine 3 conventionally includes a series of cavities 4 each ensuring the forming of a container 2. In a known manner, the containers 2 which have just been formed by the machine 3 are laid successively on an output conveyor 5 to form a line of containers. The containers 2 are transported in line by the conveyor 5 along a translational path F in order to route them successively to different treatment stations.

In accordance with one advantageous but non-exclusive arrangement of the invention, the facility 1 according to the invention is placed as close as possible to the forming machine 3 so that the output conveyor 5 ensures the successive travel of the high-temperature containers 2 in front of this inspection facility 1. Typically, the facility 1 is positioned between the output of the forming machine 3 and the annealing lehr 6, and preferably before a surface treatment hood generally constituting the first treatment stations after the forming.

The facility 1 according to the invention includes at least a first bispectral infrared camera 11 and a second bispectral infrared camera 12 disposed diametrically opposite to each other on either side of the translational path F of the containers. Each bispectral infrared camera 11, 12 is suitable for delivering images obtained from the infrared radiation of the wall of the container located in its field of observation. Each bispectral infrared camera 11, 12 delivers, for each container 2, at least one first image obtained from the infrared radiation received in a first spectral band $\lambda 1$ and at least one second image obtained from the infrared radiation received in a second spectral band $\lambda 2$. A spectral band refers to an interval of wavelengths. The characteristics of the spectral bands $\lambda 1$, $\lambda 2$ will be specified in the remainder of the description.

According to the variant illustrated in FIG. 1, the facility 1 according to the invention also includes a second pair 13, 14 of bispectral infrared cameras. These bispectral infrared cameras 13, 14 of this second pair are also disposed diametrically opposite to each other on either side of the translational path F of the containers. For example, the bispectral infrared cameras 11, 12 of the first pair are disposed such that their observation axes are at 45° relative to the translational path F. Likewise, the bispectral infrared cameras 13, 14 of the second pair are disposed at 45° relative to the translational path F so that the observation axes of the bispectral infrared cameras 11 to 14 are offset in pairs by 90°. Of course, such an arrangement of the bispectral infrared cameras is in no way limiting. To adapt to unfavorable spacing conditions between the traveling containers, the angles between the four observation axes can be adapted for example to the following values: 30°, 150°, 30°, 150°.

The invention could also operate by using three bispectral infrared cameras with their axes at 120°. In this case, it will be considered in this case that the field of each camera is divided into two portions, each field portion containing the image of a sector of 60° of the cylindrical container. Each field portion of one camera is opposite to a field portion of another camera.

The invention can finally be carried out with more than four cameras, by respecting the principle of producing bispectral infrared images from the point of view of all the walls.

The facility 1 according to the invention also comprises a system 15 for driving the operation of the bispectral infrared cameras so as to acquire images $K_1$, $K_2$ delivered by the bispectral infrared cameras according to a method which will be described in detail in the remainder of the description. The facility 1 according to the invention also includes a computer 16 configured to determine the thickness of the glass wall of the container by analyzing the images $K_1$, $K_2$ delivered by the bispectral infrared cameras 11-14.

In the present text, a computer 16 is a computer unit which can comprise, in a known manner, in particular a microprocessor, data input/output buses, memory, connections to a computer network and/or a display. The computer can be a computer unit dedicated to the facility in order to measure the wall thickness, or which can be shared with other elements of the container manufacturing line. It can for example be a centralized unit for driving the line or part of it. Among the inputs-outputs, the means for acquiring the infrared images are of course included. The means for storing the digital infrared images are included among the memory. The microprocessor is configured to execute programs organized to perform the algorithms implementing the method according to the invention.

The computer analysis of digital images produces an inspection result which can comprise a binary result (true/false, present/absent, compliant/non-compliant, etc.) and/or a qualitative even quantitative result, for example in the form of one or several measurement(s). The inspection result can therefore include not only minimum and maximum values of the glass thickness but also the distribution and vertical or horizontal deviations, as well as the location of the thin or thick areas, significant for correcting the method. In addition to the determination of a thickness distribution or mapping, therefore of a distribution of material in the inspected container, the inspection result can also include temperature mappings of the containers, the identification of the regions of high thermal stresses when locally high temperature variations are observed. In addition, this analysis can include the detection of appearance or composition defects such as the presence of inclusions, bubbles, folds or cracks on the surface, or geometric or dimensional defects such as leaning necks, external dimension deviations.

Among the outputs of the computer, communication lines can be provided in the direction of any control system of the manufacturing machine, with the aim of correcting the drifts of the method based on the performed measurements.

The following description is carried out by taking into account only the first pair of the bispectral infrared cameras 11, 12 considering that this description can be applied for the second pair of the bispectral infrared cameras. The first bispectral infrared camera 11 is disposed along a first side I of the container 2 while the second bispectral infrared camera 12 is disposed along a diametrically opposite second side II of the container.

Given that each container 2 includes a glass wall having a revolution or cylindrical shape, the diametrically opposite positioning of the bispectral infrared cameras 11, 12 relative to a container leads to consider that for each measurement point, the container 2 has a wall called front wall and a wall called rear wall, the front and rear walls for a bispectral infrared camera corresponding to the rear and front walls for the other camera. In the example illustrated more particularly in FIG. 2, each container 2 includes by convention, a first wall $2_1$ located on the first side I of the container, that is to say located closest to the first bispectral infrared camera 11 and a second wall $2_2$ located on the diametrically opposite second side II that is to say located closest to the second bispectral infrared camera 12. Thus, each bispectral infrared camera 11, 12 takes into account the radiation emitted by the front wall of the container and possibly the radiation emitted by the rear wall of the container and having passed through the front wall.

In accordance with the invention, each bispectral infrared camera 11, 12 delivers for each container at least two infrared images of the radiation of the container located in its field of observation, the one $K_1$ in a first spectral band $\lambda 1$ and the other $K_2$, in a second spectral band $\lambda 2$. This first spectral band $\lambda 1$ and this second spectral band $\lambda 2$ are chosen according to the measurement principle described below.

It should first be considered that the first spectral band $\lambda 1$ and the second spectral band $\lambda 2$ are distinct or disjoint that is to say without any common value. According to another characteristic, the absorption of the radiation by the glass is different in the two spectral bands for the temperature of the containers 2.

The theory of the thermal radiation is recalled below. In the remainder of the description, the radiation is assimilated for the sake of simplification to the infrared radiation perceived at a solid angle for an observer observing a radiating body, for example a thermal camera observing a container.

As illustrated in FIG. 3, the thermal radiation $R_{cn}$ of the black body at a given wavelength and a given temperature, $\lambda$ and T respectively, is given by the expression:

$$R_{cn}(\lambda, T) = \frac{C1}{\lambda^5} + \frac{1}{e^{C2/\lambda T} - 1} \qquad [\text{Math. 1}]$$

According to the definition of the black body, the emissivity E is, at thermal balance, equal to the absorption $\alpha$:

$$1 = \varepsilon = \alpha \qquad [\text{Math. 2}]$$

For a glass wall (gray body), the expression of the total perceived radiation M (total perceived radiation) as illustrated in FIG. 4 is written:

$$M = R + \rho + Tr \qquad [\text{Math. 3}]$$

where R is the thermal radiation, $\rho$ the reflected radiation and Tr the transmitted radiation.

In the working spectral range, therefore for the wavelength intervals perceived by the sensors according to the invention, the reflected radiation is considered negligible compared to the intensity of the radiation emitted by a container. Subsequently, the flux perceived by reflection is considered to be zero, $F = \rho = 0$.

$$M = R + Tr \qquad [\text{Math. 4}]$$

For a semi-transparent body, the Beer-Lambert law defining the absorption $\alpha$ of a radiation A as a function of the thickness e through which the radiation Ao passes, is considered.

$$Tr = \tau \times Ao = (1-\alpha) \times Ao \qquad [\text{Math. 5}]$$

where Ao is the incident radiation and $\tau$ is the transmission.

$$\varepsilon(\lambda,T,e) = \alpha(\lambda,T,e) = (1 - e^{-\mu(\lambda,T)e}) = (1 - \tau(\lambda,T,e)) \qquad [\text{Math. 6}]$$

where $\mu(\lambda T)$ is the absorption coefficient (in $mm^{-1}$) for a wavelength $\lambda$, and a given temperature T (in °K). In practice, $\mu(\lambda T)$ is the absorption coefficient integrated over a narrow wavelength band centered on a wavelength $\lambda$.

In the following, the dependencies with respect to the temperature of the emissivity and of the absorption are considered negligible, in the field of the conditions of application, that is to say for the chosen glass temperatures and wavelength intervals.

The radiation R emitted by the glass wall of thickness e and temperature T for a given wavelength $\lambda$ is written:

$$R(\lambda,T,e) = \varepsilon(\lambda,e) \times R_{cn}(\lambda,T) \qquad [\text{Math. 7}]$$

where the emissivity of the wall is expressed according to the equation [6]:

$$\varepsilon(\lambda,e) = 1 - e^{-\mu(\lambda) \cdot e} \qquad [\text{Math. 8}]$$

The application of the thermal radiation theory, according to the invention, leads to take into account for a container the two glass walls. Indeed, for a measurement point considered on the first side for example of the first wall of the container, the radiation received from the container comprises the radiation of the first wall located on the side of the measurement point plus the radiation of the second opposite wall which emits towards the inside of the container and which passes through the first wall. Thus, as illustrated in FIG. 2, the perceived radiation $M_{12}^{\lambda 1}$ of the first wall $2_1$, of thickness e1 and temperature T1 of the container in a first spectral band $\lambda 1$ sensitive to the thickness and to the temperature, includes the thermal radiation $R(\lambda 1,T1,e1)$ of said wall and the transmitted radiation $\tau(\lambda 1,e1) \cdot R(\lambda 1,T2,e2)$ which is the thermal radiation $R(\lambda 1,T2,e2)$ of the second wall $2_2$, of thickness e2 and temperature T2 at least partially absorbed by the wall $2_1$, therefore with a transmission $\tau(\lambda 1,e1)$. Similarly, the perceived radiation $M_{21}^{\lambda 1}$ of the second wall $2_2$, of thickness e2 and temperature T2 of the container in the first spectral band $\lambda 1$ sensitive to the thickness and to the temperature, includes the thermal radiation $R(\lambda 1,T2,e2)$ of said wall and the transmitted radiation $\tau(\lambda 1,e2) \cdot R(\lambda 1,T1,e1)$ of the first wall $2_1$, of thickness e1 and temperature T1 at least partially absorbed by the wall $2_2$, therefore with a transmission $\tau(\lambda 1,e2)$. In the foregoing, the transmissions $\tau(\lambda 1,e1)$ and $\tau(\lambda 1,e2)$ and for the wavelength $\lambda 1$, depend on the thickness of the traversed wall according to the equation [6], with the influence of the negligible temperature.

Similarly, as illustrated in FIG. 5, in the second spectral band $\lambda 2$ sensitive to the thickness and to the temperature, the received radiation $N_{12}^{\lambda 2}$ of the first wall $2_1$, of thickness e1 and temperature T1 of the container includes the thermal radiation emitted by said wall in the wavelength $\lambda 2$, namely $R(\lambda 2,T1,e1)$ and the radiation $\tau(\lambda 2,e1) \cdot R(\lambda 2,T2,e2)$ of the second wall $2_2$, of thickness e2 and temperature T2 at least partially absorbed by the wall $2_1$ therefore with a transmission $\tau(\lambda 2,e1)$. Similarly, the received radiation $N_{21}^{\lambda 2}$ of the second wall $2_2$, of thickness e2 and temperature T2 of the container in the second spectral band $\lambda 2$ sensitive to the thickness and to the temperature includes the radiation of said wall $R(\lambda 2,T2,e2)$ and the radiation $\tau(\lambda 2,e2) \cdot R(\lambda 2,T1,e1)$ of the first wall $2_1$, of thickness e1 and temperature T1, at least partially absorbed by the wall $2_2$ therefore with a transmission $\tau(\lambda 2,e2)$.

Given the thermal radiation theory mentioned above, it is possible to write the following equations:

$$M_{12}^{\lambda 1}=R(\lambda 1,T1,e1)+\tau(\lambda 1,e1)\cdot R(\lambda 1,T2,e2) \quad [9]$$

$$M_{21}^{\lambda 1}=R(\lambda 1,T2,e2)+\tau(\lambda 1,e2)\cdot R(\lambda 1,T1,e1) \quad [10]$$

$$N_{12}^{\lambda 1}=R(\lambda 2,T1,e1)+\tau(\lambda 2,e1)\cdot R(\lambda 2,T2,e2) \quad [11]$$

$$N_{21}^{\lambda 2}=R(\lambda 2,T2,e2)+\tau(\lambda 2,e2)\cdot R(\lambda 2,T1,e1) \quad [12]$$

These equations [9], [10], [11] and [12] relate to the considered radiations across the container, namely for two walls of thickness e1, e2 at temperature T1 and T2 respectively and separated by an air gap. It is recalled that the emissivity must be different for the wavelengths $\lambda 1$ and $\lambda 2$, otherwise the system of course only would have two equations instead of four.

The invention is based on the fact that the four equations [9] to [12] allow knowing the four unknowns, namely for two walls the thickness e1, e2 and the temperature T1 and T2 respectively, from the four radiation measurements $M_{12}^{\lambda 1}$, $M_{21}^{\lambda 1}$, $N_{12}^{\lambda 2}$ provided by measuring means such as infrared bispectral cameras observing the hot containers. The equations are as just explained, from the Planck law for the radiation and the Beer-Lambert law for the transmission. The knowledge a priori of the containers and of the material, or of the parameter identification or calibration methods, leads to accurately determine these equations for a given production of containers.

To facilitate the implementation of the invention, one method consists in simplifying the equations, which allows a simplified identification of the parameters and faster calculations in real time during the implementation of the method by means of a computer analyzing infrared images. The following will therefore define the simplified functions of emissivity, of black body radiation and of transmission with absorption, around the operating points, therefore for selected spectral bands, for the spectral transmission of the glass, for the temperature range of the containers at the output of the forming machines, therefore between 300 and 700° C., for the range of thicknesses to be measured, for example between 0.5 and 5 mm.

In accordance with the equation [7], the radiation emitted by a wall, therefore the specific radiation to a glass wall is:

$$R(\lambda 1,T1,e1)=\varepsilon(\lambda 1,e1)\times R_{cn}(\lambda 1,T1). \quad [\text{Math.13}]$$

According to the invention and according to the equation [8], the emissivity ε in the first spectral band $\lambda 1$ is a function of the thickness of the semi-transparent body. This emissivity is therefore different from 1. For values of wall thicknesses to be measured (for example 0.5 to 5 mm), the emissivity for the first spectral band $\lambda 1$ is approximated by an affined function of the thickness whose parameters are identifiable by measurement and calibration.

$$\varepsilon(e1)=(a\cdot e1+b) \quad [\text{Math.14}]$$

with the coefficients a, b depending on the wavelength $\lambda 1$.

The radiation of the black body will be described by a function $G(\lambda 1,T)$, simpler than the equation [1]. For the working wavelength $\lambda 1$, more specifically for the working spectral band centered on $\lambda 1$, $G(\lambda 1,T)=G1(T)$ is a function only of the temperature. G1(T) is a simplified model of the radiation of a black body for the spectral band $\lambda 1$, derived from the Planck law, for example it is a polynomial, power or exponential function. In practice, this function G1 takes into account the entire acquisition chain, and in particular the spectral sensitivity of the sensor and the transmission of the optical components interposed between the container and the sensor. The parameters of the function G1, for example the coefficients of the polynomial, the exponent, the exponential coefficient, etc. are determined in any appropriate manner, in particular experimentally in a phase of calibrating the measuring device according to the invention. Obviously for the second wavelength $\lambda 2$ is determined in the same way, the function $G(\lambda 2,T)=G2(T)$.

A simplified model for the radiation R emitted by a glass wall at a given wavelength or for a given spectral band around a wavelength $\lambda 1$, is therefore now written as follows:

$$R(\lambda 1,T1,e1)=R(T1,e1)=(a\cdot e1+b)\times G1(T1) \quad [\text{Math. 15}]$$

In this expression, the parameters or constants of G1(T) and the coefficients a and b can be determined experimentally, or a priori according in particular to the composition of the glass. Of course, the radiation of the same wall for a wavelength $\lambda 2$ as well as the radiation of the other wall of thickness e2 and temperature T2 are written in the same way, namely:

$$R(\lambda 1,T1,e1)=R(T1,e1)=(a\cdot e1+b)\times G1(T1) \quad [\text{Math. 15}]$$

$$R(\lambda 1,T2,e2)=R(T2,e2)=(a\cdot e2+b)\times G1(T2) \quad [\text{Math. 16}]$$

$$R(\lambda 2,T1,e1)=R(T1,e1)=(c\cdot e1+d)\times G2(T1) \quad [\text{Math. 17}]$$

$$R(\lambda 2,T2,e2)=R(T2,e2)=(c\cdot e2+d)\times G2(T2) \quad [\text{Math. 18}]$$

The transmission of a radiation coming from a rear wall by the front wall of thickness e=e1 or e2 is linearized in the following equation [19], using in particular the equations [6] and [14] around the operating point determined by a given temperature, the first spectral band centered around the first wavelength $\lambda 1$ and for the range of thicknesses to be measured:

$$\tau(\lambda 1,e)\cdot=e^{-\mu(\lambda 1)e}=1-\alpha=1-\varepsilon(e)=1-(a\cdot e+b) \quad [\text{Math. 19}]$$

Similarly, for the second spectral band centered around $\lambda 2$, the attenuation of the radiation coming from the front wall by the rear wall is:

$$\tau(\lambda 2,e)\cdot=e^{-\mu(\lambda 2)e}=1-\alpha=1-\varepsilon(e)=1-(c\cdot e+d) \quad [\text{Math. 20}]$$

The coefficients a and b, c and d are obtained by calibration or known a priori by any suitable method. They depend on an operating point, in particular on the chosen wavelengths $\lambda 1$ and $\lambda 2$ and on the temperature area of the containers inspected and on the range of thicknesses to be measured.

For the wavelength $\lambda 1$, the radiation $M_{12}^{\lambda 1}$ corresponds to the total radiation of the first wall plus the radiation of the second wall modulated by the absorption of the first wall. It can therefore be expressed as follows:

$$M_{12}^{\lambda 1}=(a\cdot e1+b)\times G1(T1)+(1-(a\cdot e1+b))\times(a\cdot e2+b)\times G1(T2) \quad [\text{Math.21}]$$

Likewise, the radiation $M_{21}^{\lambda 1}$ corresponds to the total radiation of the second wall plus the radiation of the first wall modulated by the absorption of the second wall. It can therefore be expressed as follows:

$$M_{21}^{\lambda 1}=(a\cdot e2+b)\times G1(T2)+(1-(a\cdot e2+b))\times(a\cdot e1+b)\times G1(T1) \quad [\text{Math.22}]$$

Similarly for the wavelength $\lambda 2$, the radiation $N_{12}$ corresponds to the total radiation of the first wall plus the radiation of the second wall modulated by the absorption of the first wall. $N_{12}$ can therefore be expressed such that:

$$N_{12}^{\lambda 2}(c\cdot e1+d)\times G2(T1)+(1-(c\cdot e1+d)\times(c\cdot e2+d)\times G2(T2) \quad [\text{Math.23}]$$

Similarly, $N_{12}^{\lambda 2}$ can therefore be expressed such that:

$$N_{21}^{\lambda 2}=(c \cdot e2+d) \times G2(T2)+(1-(c \cdot e2+d)) \times (c \cdot e1+d) \times G2(T1)$$ [Math.24]

In this first variant of the invention, if the second spectral band λ2 is chosen so that the emissivity, although different from that for the first spectral band λ1, depends on the thickness, then the equations [9], [10], [11] and [12] can be replaced respectively by the equations [21], [22], [23] and [24].

In a complementary manner, the following considerations must be taken into account in particular because of the characteristics presented by the containers 2 exiting the forming machine.

It should be noted as well that, in a determined wavelength range, the emissivity of the glass is very little sensitive to the temperature of the wall which varies between 300 and 700° C. For this determined wavelength range, the absorption coefficient (therefore the emissivity) does not depend on the temperature, or this dependence is negligible. Thus, only the spectral absorption coefficient μ relates the absorption to the thickness and similarly relates the emissivity to the thickness.

According to one characteristic of the invention, the first spectral band λ1 is chosen from this wavelength range for which the emissivity of the glass does not depend on the temperature. This allows applying the equations [7] and [8].

In addition, for a spectral band determined in a range greater than 4,500 nm and preferably greater than 5,000 nm, the emissivity of the glass is very close to 1, that is to say considered equal to 1 by approximation. For this spectral band, the radiation is assimilated to that of the black body. According to a preferred variant, the second spectral band λ2 is chosen in this wavelength range, for which the radiation does not depend on the thickness, for which the observed wall does not transmit the radiation of the opposite face, since the absorption is also close to 1, in other words the glass is opaque in this wavelength range. The expressions of the radiation perceived in this spectral band, for each face of the wall, will be deduced, namely:

$$N_1=R(\lambda 2,T1,e1)=G(T1)$$ [Math.25]

$$N_2=R(\lambda 2,T2,e2)=G(T2)$$ [Math.26]

In this variant, therefore, the equations [9], [10], [11] and [12] can be replaced respectively by the equations [21], [22], [25] and [26]. This variant using a wavelength in which the radiation does not depend on the thickness simplifies the calculations to solve the system of 4 equations with 4 unknowns since the unknowns T1 and T2, therefore the temperatures of the two walls, immediately arise from the equations [21] and [22].

In accordance with the invention, the first spectral band λ1 is chosen so that in the first spectral band, the absorption of the radiation by the glass is such that:

the radiation measured from the first side of the container 2, coming from the first wall $2_1$, is the sum of the radiation emitted by the first wall $2_1$ and of the radiation emitted by the second wall $2_2$ and transmitted with absorption through the first wall $2_1$, such that said combined radiation depends on the thicknesses and temperatures of the first and second walls, and the radiation measured from the second side of the container 2, coming from the second wall $2_2$, is the sum of the radiation emitted by the second wall $2_2$, and of the radiation emitted by the first wall $2_1$ and transmitted with absorption through the second wall $2_2$, such that said combined radiation depends on the thicknesses and temperatures of the first and second walls.

It should be understood that the invention proposes to measure the infrared radiation with a first spectral band λ1 at which the intensity of the radiation depends on the thickness of the glass wall and on the surface temperature of the wall. According to the invention, the first spectral band λ1 is chosen so that the emissivity depends on the thickness of the wall therefore far from 1, but also high enough for a sufficient radiation to be measured. It is furthermore sought for this emissivity to vary little with the tint of the glass. Thus, this first spectral band λ1 is chosen so that the emissivity varies for example between (approximately) 0.3 and 0.7 for the white glass when the thickness varies between 1 and 5 mm, for glass temperatures around 450° C., more broadly between 300 and 700° C. It should be noted that the emissivity for the same thickness and the same temperatures in green or amber glass varies around the same values.

Furthermore, this first spectral band λ1 is chosen to obtain a transmission, with absorption by the front face, of the radiation coming from the rear face. This indeed allows that in the equations [10] and [11], the transmissions respectively $\tau(\lambda 1,e1)=e^{-\mu(\lambda 1)e1}$ and $\tau(\lambda 1,e2)e^{-\mu(\lambda 1)e2}$ are not equal to 1, therefore the attenuation is not zero. Zero attenuation would not correspond to a normal container. With zero attenuation, only the sum of the thicknesses e1+e2 of the two walls without differentiating the two could be measured. Conversely, if the absorption is total $e^{-\mu(\lambda 1)e1}=0$ or $e^{-\mu(\lambda 1)e2}=0$, this means that the glass is opaque for the first spectral band. In this case, only the surface temperature of the front wall would be measured in this first spectral band, regardless of the thickness.

It should be noted that the radiation emitted by the container in the first spectral band λ1 can be chosen from a range between 1,100 nm and 2,600 nm. However, this range is suitable for green glass or amber glass containers but not for white glass containers because in this range the emissivity of white (transparent) glass is very low.

In accordance with the invention, the first spectral band λ1 is chosen from a range between 2,800 nm and 4,000 nm and preferably between 3,000 nm and 4,000 nm. This preferred first spectral band is chosen to operate for a large number of glass tints, including the white glass.

As indicated above, the second spectral band λ2 is chosen such that the absorption of the radiation by the glass is different from that of the first spectral band λ1. It is recalled that the emissivity varies between 0.3 and 0.7 for the first spectral band λ1 chosen. According to a first variant illustrated in FIG. 5, the second spectral band λ2 is also chosen such that the radiation measured, on the one hand, from the first side of the container, coming from the first wall $2_1$ is the sum of the radiation emitted by the first wall $2_1$ and of the radiation emitted by the second wall $2_2$ and transmitted through the first wall, and on the other hand, from the second side of the container, coming from the second wall $2_2$ is the sum of the radiation emitted by the second wall $2_2$ and of the radiation emitted by the first wall $2_1$ and transmitted through the second wall $2_2$, the combined radiation being dependent on the thicknesses of the walls and the temperatures of the walls.

According to this first variant, the radiation emitted by the container in the second spectral band λ2 is chosen from a range between 1,100 nm and 2,600 nm. In this variant, the transmission is high and the emissivity may be low for some glasses, typically less than 0.1 for glass thicknesses of 1 to 5 mm at 450° C. Since the infrared signal is restricted, the accuracy in the measurement of the thickness may be insufficient for these glass tints.

According to a second preferred variant illustrated in FIG. 6, the second spectral band λ2 is chosen such that the absorption of the radiation by the glass is such that the radiation measured on the one hand, from the first side I of the container, coming from the first wall $2_1$ is the radiation emitted only by the surface of the first wall $2_1$ and on the other hand, from the second side II of the container, coming from the second wall $2_2$ is the radiation emitted only by the surface of the second wall, said radiation depending only on the temperature.

Thus, the radiation $N_1^{\lambda 2}$ emitted by the first wall of the container in the second spectral band is sensitive to the surface temperature only. Likewise, the radiation $N_2^{\lambda 2}$ emitted by the second wall of the container in the second spectral band is sensitive to the surface temperature only.

According to this preferred variant, the second spectral band λ2 is chosen from a range greater than 4,500 nm and preferably greater than 5,000 nm. The second spectral band λ2 is chosen so that the emissivity is close to 1, that is to say close to that of the black body. This means that the absorption of the radiation by the glass in this spectral band is high so that the emissivity is for example greater than 0.9. The radiation N1, N2 perceived in the second spectral band λ2 for the first face and for the second face is quite faithfully represented by Planck law or the approximation function according to the invention G(T1) and G(T2), as indicated by the equations [25] and [26].

According to this preferred variant with the second spectral band λ2 chosen in a range greater than 4,500 nm and preferably greater than 5,000 nm, it is advantageous to simultaneously choose the first spectral band λ1 in a range between 2,800 nm and 4,000 nm and preferably between 3,000 nm and 4,000 nm. Thus, it becomes possible to measure or produce images in the two spectral bands λ1 and λ2, to use one and the same sensor technology, of the MWIR (Medium Wave InfraRed), preferably uncooled, sensor type. A cooled sensor here designates the MWIR or LWIR sensors such as those marketed by the SOFRADIR or LYNRED companies which are equipped with cryogenic type cooling systems. An uncooled sensor is indeed much cheaper than a cooled sensor, it is more robust. Of course, the MWIR cameras according to the invention are equipped with solutions for the protection of the radiations (cooled enclosure, skylight, screen) and for the cooling and/or heat dissipation such as for example: water circuits, forced ventilation, Peltier effect cells, heat pipes, radiators, etc.

Typically, the first spectral band λ1 is chosen from a range between 3,000 nm and 4,000 nm and the second spectral band λ2 is chosen from a range greater than 4,500 nm. Advantageously, the first spectral band λ1 is chosen centered around a wavelength value on the order of 3,600 nm while the second spectral band λ2 is chosen centered around a wavelength value on the order of 4,700 nm.

In accordance with the invention, the bispectral infrared cameras 11-14 are driven by the system 15 so as to measure, from the first side I of the container, the intensity of the radiation coming from the first wall $2_1$ in the first spectral band λ1 and simultaneously in the second spectral band λ2 and from the second side II of the container, the intensity of the radiation coming from the second wall $2_2$ in the first spectral band λ1 and simultaneously in the second spectral band λ2. Thus, for each container 2, the invention aims to perform at least two measurements of the intensity of the radiation received from two opposite walls, in a first spectral band, and at least two measurements of the intensity of the radiation from two opposite walls, in a second spectral band. According to one advantageous characteristic, the invention aims to produce, as a radiation measurement, one-dimensional or two-dimensional images of the walls of the containers. Thus, the bispectral infrared cameras 11, 14 each deliver, for each container, at least two infrared images of the radiation of the container wall located in its field of observation. According to one variant, the two bispectral infrared cameras 11, 12 deliver for each container, at least two images of the infrared radiation in the first spectral band and at least two images of the infrared radiation in the second spectral band. According to another variant implementing four bispectral infrared cameras 11, 14, eight images of the infrared radiation can be obtained so that the wall of the container as a whole is represented in the two spectral bands. In this case, the observed field is such that each camera measures at least a quarter of the circumference of the container.

It can also be envisaged to increase the overlap of the views, by means of three pairs of opposite bispectral cameras. More generally, any arrangement of the cameras can be provided based on the shape and the spacing of the containers, in order to fully observe the circumference of the containers, whether their shape is characterized by a circular horizontal (cone-shaped body or ordinary cylinder) or rectangular, polygonal planar section, etc. in accordance with the practices of those skilled in the art and in particular according to the structure of the in-line inspection systems in the cold sector.

In accordance with another characteristic of the invention, the computer 16 allows determining at least the thickness e1 of the first wall $2_1$ and the thickness e2 of the second wall $2_2$, from the measurements of the intensity of the radiation coming from the first wall $2_1$ in the first and second spectral bands and from the second wall $2_2$ in the first and second spectral bands, by taking into account in the intensity of the radiation in the first spectral band, the radiation emitted by a wall and the radiation transmitted with absorption, and coming from the other diametrically opposite wall.

Thus, the thickness e1 of the first wall $2_1$ and the thickness e2 of the second wall $2_2$ are determined from the four measurements of the radiation intensity, according to the general equations [9], [10], [11] and [12], or more specifically their simplification [21], [22], [23] and [24], or even [21], [22], [25] and [26] when the second wavelength is chosen such that the emissivity is close to 1. This system of four equations with four unknowns is solved at least in the linearized versions, but also with more complex models if necessary in order to increase the measurement accuracy.

According to the preferred variant for which the second spectral band λ2 depends only on the temperature, the thicknesses and possibly the temperatures are determined from the system of equations [21], [22], [25] and [26].

It is recalled that for this preferred variant, the infrared radiation is measured on the one hand with a first spectral band at which the intensity of the radiation depends on the thickness of the wall and on the surface temperature and on the other hand with a second spectral band at which the intensity of the radiation depends only on the surface temperature. Thus, the temperature information can be "subtracted from the signal".

From the four independent measurements of the radiation and by taking into account, in the first spectral band, the influence of the opposite face on the radiation perceived for each face, it is possible to deduce the thickness e1 of the first face, the thickness e2 of the second face and optionally, the temperature T1 of the first face and the temperature T2 of the second face. To perform this calculation, a mathematical model is used linking the four radiation measurements and the four final measurements, namely the two thickness measurements and the two temperature measurements.

This mathematical model can be empirical or analytical. It may only be valid for some operating conditions allowing setting constants and linearizing the model. Of course, the simplifications made to the equations [15] and [19] are not essential to the invention, they simply allow an easier and less expensive implementation of the calculations. The analytical model can be obviously more elaborate, allowing more accurate measurements, and can take into account the composition, the average temperatures or the shape of the containers. The mathematical model can also include a geometric model able to describe the 3D geometry of a container, having as characteristics a distribution of glass thickness and a distribution of temperature. For example, for a simple conical-type item, the surface of the body would be a cone whose each point has a thickness value in mm and a temperature in K.

It appears from the description that the facility 1 according to the invention includes bispectral infrared cameras 11-14. Although non-planar image sensors can be employed without inconvenience to carry out the invention from non-planar images, the description assumes planar sensors and the term formed image generally means a planar image of an object or a scene, in this case at least part of the wall of a container.

When there are several sensors per camera, then there are several ways to assemble them. In what follows, the upstream and the downstream specify the position of the optical elements placed on the radiation beams collected and processed in the direction of path of the light originating from the container to reach a sensor.

According to a first variant of the invention, a bispectral infrared camera comprises, as illustrated for example in FIGS. 7, 8:
- a beam splitter 20, downstream of which the rays are separated into two distinct downstream beams;
- downstream of the beam splitter 20, two distinct sensors 21, 22 (FIG. 7) or two sensor portions (FIG. 8), placed in a plane or two image planes, each receiving one of the two distinct downstream beams, the first sensor or the first sensor portion receiving a first radiation beam in the first spectral band and the second sensor or the second sensor portion receiving a second radiation beam in the second spectral band;
- the first and second beams being shaped upstream or downstream of the splitter 20, by a lens 23 forming by optical conjugation on each image plane, therefore each sensor or sensor portion, an optical image $K_1$, $K_2$ of the container in respectively the first spectral band and the second spectral band;
- the first and/or the second beam being filtered by one or several optical filters, for example of the band pass type 25, 26 selecting respectively the first spectral band and the second spectral band.

The at least two distinct sensors 21, 22 (FIG. 7) or sensor portions (FIG. 8), each deliver from each container a digital image corresponding to the conversion of the optical images $K_1$, $K_2$ of the radiation M or N perceived in at least two distinct infrared wavelength bands.

The beam splitter 20 is for example a prism, a blade or a splitter cube. It is an optical component deflecting an upstream optical beam along two downstream optical beams in two different directions.

A linear sensor portion is a line of juxtaposed photosensitive elements. The acquisition or the reading of a linear sensor portion provides a single digital image line. Also, during the inspection of moving containers, it is known to acquire the successive digital image lines in order to reproduce, by the simple and known scanning method, a two-dimensional image of a container passing through the planar field of a linear sensor portion. (nb planar field=defined by sensor line and optical center=fan-type field). Of course, the displacement or travel vector is not parallel to the direction of the linear sensor portion. There are linear sensors on the market including a single line of photosensitive elements. There are also sensors including several lines of juxtaposed photosensitive elements and delivering as a signal only digital image lines which are combinations of the information from the different lines. Finally, a matrix sensor can be driven so as to acquire only one or two or more digital image lines coming from distinct lines of the sensor, and from these distinct lines juxtaposed over time, obtain by scanning one or two or more 2D images of the moving container, separated in time, corresponding to different positions. In other words, a matrix sensor can be used as one or two or more linear sensors, it delivers digital image lines over time. The notion of linear sensor portion covers both methods.

According to a second variant of the invention, each bispectral infrared camera comprises, as illustrated for example in FIG. 9:
- a lens 23 forming by optical conjugation on a sensor plane, an optical image $K_3$ of a field through which a container passes;
- two distinct linear sensor portions 41, 42, with their support lines $s_1$, $s_2$ being vertical and disposed such that during the travel of a container in the field of a lens 23, a scanning image is produced with each of the two linear sensor portions;
- the first linear sensor portion 41 receiving a first radiation beam portion 31 in the first spectral band;
- the second sensor portion 42 receiving a second radiation beam portion 32 in the second spectral band;
- at least one optical filter 45 disposed on the path of the light beams between the lens and the two linear sensor portions 41, 42 to select the first spectral band and the second spectral band.

It is noted that the beam splitter 20 is not required in this version.

In this way, after a container has passed through the field of the lens 23, it has passed through the field of each of the two linear sensor portions. By scanning, two two-dimensional images of the container are obtained in the two chosen wavelengths.

One advantageous embodiment is to use a single two-dimensional sensor 43, placed behind at least one optical filter covering only one part of the sensor, as illustrated in FIG. 9. Another way consists in placing two linear sensors in the image plane.

Of course in this second variant, nothing prevents that, during the travel of a container in the field of the lens 23, its two-dimensional image is, at a given point, partly formed on the first and partly on the second sensor portion 41, 42.

In all the variants, possibly, two optical filters are used to select these two spectral bands. It may be advantageous to choose band-pass filters as optical filters.

It is clear that at least one filter is needed, only if the two sensor portions are of the same technology, accordingly each with the same intrinsic spectral response or sensitivity.

According to one preferred variant in which the second spectral band λ2 is chosen in a range greater than 4,500 nm and preferably greater than 5,000 nm, and the first spectral band λ1 in a range between 2,800 nm and 4,000 nm and preferably between 3,000 nm and 4,000 nm, one or two sensors of the MWIR (Medium Wave InfraRed) sensor type which do not require any cooling system as explained above can be used for the sensor(s). This allows carrying out the variants illustrated in FIGS. 8 and 9 comprising a single sensor. To achieve variants including two sensors, as illustrated in FIG. 7, the use of two sensors of the same technology simplifies the implementation in particular by allowing the two sensors to have the same resolution for the same field and to be synchronous, with common and simplified drive means.

The sensor(s) included in each bispectral infrared camera are for example based on PbSe at 196 or 300° K or micro bolometers.

Of course, the invention is not limited to the bispectral camera embodiments described above.

The invention claimed is:

1. A method for measuring a thickness of high-temperature glass containers (2) exiting forming cavities, the method comprising the following steps:

measuring from a first side (I) and a second side (II) of the container diametrically opposite to each other, an intensity of radiation emitted by each container (2), said radiation being emitted by a first wall ($2_1$) of the container located along the first side (I) and a diametrically opposite second wall ($2_2$) of the container located along the second side (II);

measuring radiation emitted by each container (2) in a first spectral band ($\lambda 1$) in a range between 2,800 nm and 4,000 nm and in a second spectral band ($\lambda 2$), wherein the first and second spectral bands are distinct and selected such that absorption of the radiation by glass of each container is different in the first and second spectral bands for a temperature of the containers; and at least in the first spectral band ($\lambda 1$), the absorption of the radiation by the glass of each container is such that:

the radiation measured from the first side (I) of the container, coming from the first wall ($2_1$), is a first sum of the radiation emitted by the first wall ($2_1$) and of the radiation emitted by the second wall ($2_2$) transmitted with absorption through the first wall ($2_1$), such that the first sum of radiation depends on thicknesses and temperatures of the first and second walls ($2_1$, $2_2$); and the radiation measured from the second side (II) of the container, coming from the second wall ($2_2$), is a second sum of the radiation emitted by the second wall ($2_2$) and of the radiation emitted by the first wall ($2_1$) and transmitted with absorption through the second wall ($2_2$), such that the second sum of radiation depends on thicknesses and temperatures of the first and second walls ($2_1$, $2_2$);

wherein the measuring from the first side (I) of the container of the intensity of the radiation coming from the first wall ($2_1$) in the first spectral band ($\lambda 1$) and in the second spectral band ($\lambda 2$) is simultaneous with the measuring from the second side (II) of the container of the intensity of the radiation coming from the second wall ($2_2$) in the first spectral band ($\lambda 1$) and in the second spectral band ($\lambda 2$); and determining at least a thickness of the first wall ($2_1$) and of the second wall ($2_2$), from the measurements of the intensity of the radiation coming from the first wall in the first and second spectral bands and from the second wall in the first and second spectral bands, the intensity of the radiation in the first spectral band being a sum of radiation emitted by one wall of the container, and radiation transmitted with absorption coming from the other diametrically opposite wall of the container.

2. The method according to claim 1, wherein for the second spectral band ($\lambda 2$), absorption of the radiation by the glass is different from that of the first spectral band ($\lambda 1$), and is such that:

the radiation measured from the first side (I) of the container, coming from the first wall ($2_1$) is a third sum of the radiation emitted by the first wall ($2_1$) and of the radiation, which is emitted by the second wall ($2_2$) then transmitted through the first wall ($2_2$), and the radiation measured from the second side of the container, coming from the second wall ($2_2$) is a fourth sum of the radiation emitted by the second wall ($2_2$) and of the radiation emitted by the first wall ($2_1$) and transmitted through the second wall, each of the third and fourth sums of radiation being dependent on the thicknesses of the first and second walls ($2_1$, $2_2$) and temperatures of the first and second walls ($2_1$, $2_2$).

3. The method according to claim 1, wherein temperatures ($T_1$, $T_2$) of the first wall ($2_1$) and of the second wall ($2_2$) are also determined from the measurements of the intensity of the radiation of the first wall ($2_1$) in the first spectral band and the second spectral band and of the second wall ($2_2$) in the first spectral band and the second spectral band, based on the intensity of the radiation in the first spectral band, radiation transmitted with absorption, and coming from the wall located on the other side.

4. The method according to claim 1, wherein the radiation emitted by the container in the first spectral band ($\lambda 1$) is measured in a range between 3,000 nm and 4,000 nm.

5. The method according to claim 1, wherein for the second spectral band ($\lambda 2$), the absorption of the radiation by the glass is such that:

the radiation measured from the first side (I) of the container, coming from the first wall ($2_1$), is the radiation emitted only by a surface of the first wall ($2_1$), and the radiation measured from the second side (II) of the container, coming from the second wall ($2_2$), is the radiation emitted only by a surface of the second wall ($2_2$), the radiation depending only on temperature of the first and second walls ($2_1$, $2_2$).

6. The method according to claim 5, wherein temperatures ($T_1$) of the first wall ($2_1$) and of the second wall ($2_2$) are determined from respective measurements of the intensity of the radiation of the first wall ($2_1$) in the second spectral band ($\lambda 2$) and of the second wall ($2_2$) in the second spectral band ($\lambda 2$).

7. The method according to claim 5, wherein the radiation emitted by the container in the second spectral band ($\lambda 2$) is measured in a range greater than 4,500 nm.

8. The method according to claim 5, wherein the radiation emitted by the container in the second spectral band ($\lambda 2$) is measured in a range greater than 5,000 nm.

9. The method according to claim 1, wherein the radiation emitted by the container in the second spectral band ($\lambda 2$) is measured in a range between 1,100 nm and 2,600 nm.

10. The method according to claim 1, wherein the simultaneous measurement of intensity uses at least two bispectral infrared cameras (11, 12-13, 14) each delivering, for each container, at least two infrared images of the radiation of the wall of the container located in a field of observation of each bispectral infrared camera.

11. A facility for measuring thickness of walls of high-temperature glass containers (2) exiting forming cavities (4) and moving along a translational path (F), the facility including:
- at least first (11) and second (12) bispectral infrared cameras disposed diametrically opposite to each other on either side of the translational path (F) of the containers to receive radiation emitted by a first wall ($2_1$) of each container (2) located on a first side (I) of the container and a second wall ($2_2$) of each container located on a diametrically opposite second side, each of the at least first and second bi-spectral cameras (11, 12) delivering two images of infrared radiation of the wall of the container located in a camera field of observation in a first spectral band ($\lambda 1$) in a range between 2,800 nm and 4,000 nm and in a second spectral band (2),
- the first and second spectral bands being distinct and selected such that absorption of the radiation by glass of each container is different in the first and second spectral bands ($\lambda 1$, $\lambda 2$) for a temperature of the containers; and
- at least in the first spectral band ($\lambda 1$), absorption of the radiation by the glass is such that:
  - the radiation measured from the first side of the container, coming from the first wall ($2_1$), is a first sum of the radiation emitted by the first wall ($2_1$) and of the radiation emitted by the second wall ($2_2$) and transmitted with absorption through of the first wall ($2_1$), such that the first sum of radiation depends on thicknesses and temperatures of the first and second walls ($2_1$, $2_2$); and
  - the radiation measured from the second side (II) of the container, coming from the second wall ($2_2$), is a second sum of the radiation emitted by the second wall ($2_2$) and of the radiation emitted by the first wall ($2_1$) and transmitted with absorption through the second wall ($2_2$), such that the second sum of radiation depends on the thicknesses and temperatures of the first and second walls ($2_1$, $2_2$);
- a system (15) for driving operation of the at least first and second bispectral infrared cameras (11,12) so as to acquire simultaneously, with one of the at least first and second bi-spectral cameras (11), two images measuring intensity of the radiation of the first wall ($2_1$) in the first spectral band ($\lambda 1$) and in the second spectral band ($\lambda 2$) and with another of the at least first and second bi-spectral cameras (12), two images measuring the intensity of the radiation of the second wall ($2_2$) in the first spectral band ($\lambda 1$) and in the second spectral band ($\lambda 2$); and
- a computer (16) configured to determine at least thicknesses ($e_1$, $e_2$) of the first wall ($2_1$) and of the second wall ($2_2$), by analyzing the two images giving respectively measurements of the intensity of the radiation coming from of the first wall ($2_1$) in the first spectral band ($\lambda 1$) and the second spectral band ($\lambda 2$) and the two images of the second wall in the first spectral band and the second spectral band, the intensity of the radiation in the first spectral band being a sum of the radiation emitted by a wall of the container and radiation transmitted with absorption, and coming from the wall located on the other side of the container.

12. The facility according to claim 11, characterized in that each of the at least first and second bispectral infrared cameras (11-14) includes:
- a beam splitter (20), downstream of which rays are separated into first and second distinct downstream beams; and
- first and second sensors (21, 22) or first and second sensor portions, downstream of the beam splitter (20) and placed in a plane or two image planes, each first or second sensor or sensor portion receiving one of the first and second distinct downstream beams, the first sensor or the first sensor portion receiving a first radiation beam in the first spectral band and the second sensor or the second sensor portion receiving a second radiation beam in the second spectral band;
- the first and second downstream beams being shaped upstream or downstream of the beam splitter (20), by a lens (23) forming, by optical conjugation on each image plane, an optical image (K1, K2) of the container in respectively the first spectral band and the second spectral band;
- the first and/or the second downstream beam being filtered by one or several optical filters (25, 26) selecting respectively the first spectral band and the second spectral band.

13. The facility according to claim 12, wherein the optical filter(s) (25, 26, 45) select the first spectral band in a range between 2,800 nm and 4,000 nm and the second spectral band in a range greater than 4,500 nm.

14. The facility according to claim 13, wherein the second spectral band in a range greater than 5,000 nm.

15. The facility according to claim 11, characterized in that each of the at least first and second bispectral infrared cameras each comprises:
- a lens (23) forming, by optical conjugation on a sensor plane, an optical image (K3) of a field through which a container passes;
- first and second linear sensor portions (41, 42), with respective support lines ($s_1$, $s_2$) being vertical and disposed such that during travel of a container in the field of the lens (23), a scan image is produced with each of the first and second linear sensor portions, the first linear sensor portion (41) receiving a first radiation beam portion (31) in the first spectral band, and the second linear sensor portion (42) receiving a second radiation beam portion (32) in the second spectral band; and
- at least one optical filter (45) disposed on a path of light beams, to select the first spectral band and the second spectral band.

* * * * *